US005760898A

United States Patent [19]
Haley et al.

[11] Patent Number: 5,760,898
[45] Date of Patent: Jun. 2, 1998

[54] LASER DETECTION OF EXPLOSIVE RESIDUES

[75] Inventors: Lawrence V. Haley, Ottawa; Govindanunny Thekkadath, Nepean, both of Canada

[73] Assignee: IDS Intelligent Detection Systems Inc., Ontario, Canada

[21] Appl. No.: 778,236

[22] Filed: Jan. 8, 1997

[51] Int. Cl.$^6$ .......................... G01J 3/443; G01N 21/63
[52] U.S. Cl. .......................................................... 356/318
[58] Field of Search .............................. 356/317, 318, 356/417

[56] References Cited

U.S. PATENT DOCUMENTS

| | | | |
|---|---|---|---|
| 5,098,640 | 3/1992 | Gozani et al. | 376/166 |
| 5,364,795 | 11/1994 | Sausa et al. | 436/106 |
| 5,638,166 | 6/1997 | Funsten et al. | 356/311 |

OTHER PUBLICATIONS

Ostmark, et al., "Laser Ignition of Explosives: Effects of Laser Wavelength on the Threshold Ignition Energy," Journal of Energetic Materials, vol. 12, 63–83 (1994), pp. 63–83.

Lang, et al., "Detonation of Insensitive High Explosives by a Q–Switched Ruby Laser," Applied Physics Letters, vol. 19, No. 11, Dec. 1, 1971, pp. 473–475.

Harrach, Robert J., "Estimates on the Ignition of High–Explosives by Laser Pulses," Journal of Applied Physics, vol. 47, No. 6, Jun. 1976, pp. 2743–2482.

Ostmark, et al., "Laser Ignition of Explosives: Effects of Gas Pressure on the Threshold Ignition Energy," Journal of Energetic Materials, vol. 8/4, 1990, pp. 308–322.

Primary Examiner—F. L. Evans
Attorney, Agent, or Firm—Scully, Scott, Murphy & Presser

[57] ABSTRACT

A laser is used in the detection of explosives residue by creating micro-detonations of explosive particles adhered to objects. An object is scanned with a beam of coherent laser light to induce micro-detonations of micro-particles of explosive residue adhered to the object. Temporal and spectral information representative of light emitted by the micro-particles is used to characterize the explosives.

2 Claims, 1 Drawing Sheet

LASER DETECTION OF EXPLOSIVE RESIDUES

BACKGROUND OF THE INVENTION

There is at present a need for the rapid detection of explosive residues in fingerprints left on the surfaces of carry-on or hold baggage in airports. The presence of such fingerprints on luggage is a good indication that the luggage may be suspicious in that it could contain a terrorist bomb since explosive residues are very rarely found in fingerprints. Various ways have been proposed for the detection of such residues. One frequently used technique is to take a sample wipe of the surface to be tested and then to chemically analyze the wipe sample. Another way of transferring the sample is by vacuuming the surface and transferring the particles directly into the analyzer. The chemical analysis is usually done with the aid of a gas chromatographic column and an appropriate detector like the ECD or the IMS. Even though this technique can detect picogram quantities of explosives in principle, the overall sensitivity of the system is limited by the efficiency of sample transfer from the source into the sample vaporizer in the analyzer. This sample transfer takes tens of seconds to accomplish when a sample wipe is taken, prolonging the overall detection time.

Laser interaction with explosives have been investigated before by several groups but with vastly different aims. The effect of gas pressure on the threshold ignition energy of PETN and RDX was investigated using a $CO_2$ laser by H. Ostmark and R. Grans of the Swedish Defense Research Establishment in Stockholm. They looked at the light emission from the explosives when ignited in order to establish the time of start of detonation.

SUMMARY OF THE INVENTION

A more efficient way of detecting the microparticles contained in the fingerprints or lodged on surfaces is an in-situ analysis of the microparticles, which would eliminate any physical transfer of the sample into the detector. This in turn would decrease the sampling time and avoid the sample transfer inefficiencies of the wipe or vacuum method of sampling. The present invention proposes a simple and fast way of detecting explosives by using a laser beam to interact with the explosive particles on the surface and electro-optically analyzing the results.

In the remote detection of explosives using laser pyrolisis, a pulsed laser light is used to remotely detect explosive laden fingerprints. The technique is based on the fact that microparticles of explosives like RDX and PETN are detonated when supplied with energy in the form of heat or photons or phonons. Interaction of the same type with ordinary materials produce quite different results thus giving us a way of distinguishing explosives from other materials.

DESCRIPTION OF THE PREFERRED EMBODIMENT

Figure 1:
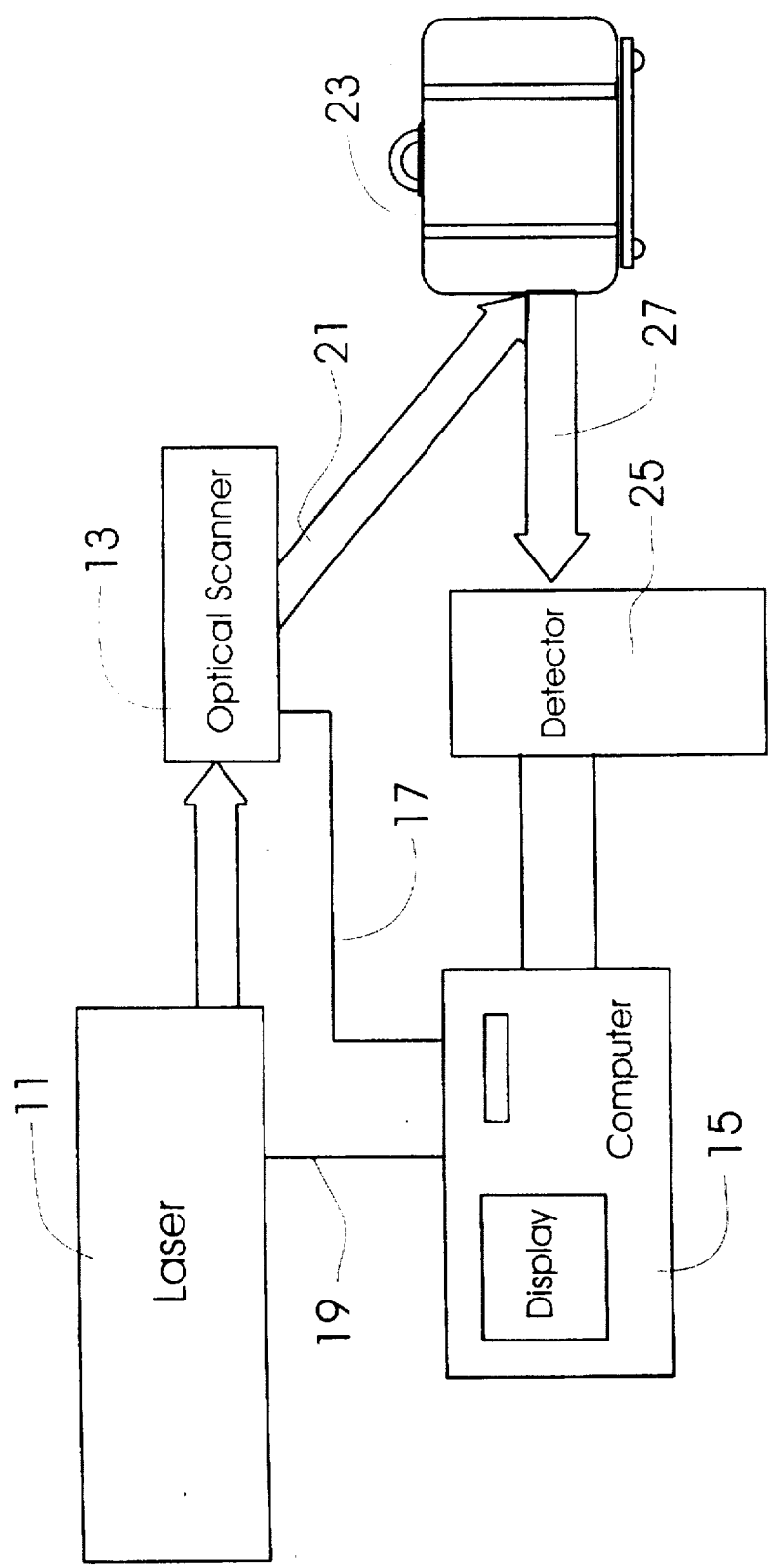
FIG. 1 is a diagramatic illustration of the apparatus for the remote sensing of explosive residues.

The method of the present invention utilizes a pulsed $CO_2$ laser as the source of energy for activating the explosives in the fingerprints. Microparticles of explosives on surfaces or in fingerprints left on the surface of a piece of luggage or other object to be tested are selectively detonated by adjusting the power and timing characteristics of the laser output. The result of such a detonation yields a light pulse which can be spectrally analyzed and converted into an electrical pulse. The characteristics of the light pulse is then be used to characterize the explosives. The laser beam can be scanned across the surface to be investigated using computer controlled mirrors. The light emitted can be remotely picked up using a telescope or picked up using a fiber-optic link to the detector. The results can be calculated and displayed in real time.

As illustrated in FIG. 1, the laser 11 is preferably a pulsed $CO_2$ laser but other types of lasers, either continuous with electronically or mechanically chopped output, or lasers with other wavelengths like the Nd YAG laser, could be used. The light is directed at the object using an optic guide 13. This guide 13 may be either a system of lenses to direct and focus the laser beam or a fiber-optic guide or a combination of both. The optic guide 13 also has the ability to direct its output to any part of the object 23 under test by means of electromechanical control, such as x-y scanning. The sweep rate and resolution of the laser beam 21 are controlled by computer 15 via signal bus 17. The intensity, duration, and repetition rate of the laser pulse are controlled by computer 15 over signal bus 19. These parameters are decided on the basis of previous empherecially derived data from test objects. They can also be controlled in real time by computer 15 based on the feedback of signals from the object surface by algorithms programmed into the computer.

Sensor 25 accepts and analyses the emmitted light radiation 27 from the laser-surface interaction. The interaction of the laser pulse with the surface will typically result in the emission of electromagnetic radiation 27 in the form of light and heat. This is picked up either remotely by sensor 25 using an adjustable optical assembly or transported to the sensor by means of an appropriate fiber optic guide. Sensor 25 can analyze the temporal and spectral information contained in the light pulse 27 and convert them into electrical signals. This is done using a frequency analyzer (typically diffraction gratings covering the appropriate frequency ranges) and a pulse analyzer (typically a photomultiplier tube or a charge coupled device array). The signal frequency range would span the infra-red to the ultraviolet. The temporal resolution of the pulse analyzer would be in the tens of nanoseconds range. When a charge coupled device array (CCD array) is used it is possible to simultaneously analyze a range of wavelengths. The outputs of the analyzer are then converted into digital pulses suitable for handling by computer programs as a data aquisition signal.

Analysis of the sensor output or data aquisition signal by the computer 15 is carried out by matching patterns of parameters that are characteristic of the explosive contamination. When ordinary surfaces are exposed to the pulsed laser light the resulting signal is typically of a slow rise time and weak to none at all. This is indicative of slow burning or no burning. Preferably the laser parameters are adjusted so as to give no appreciable signal when ordinary surfaces (like vinyl, leather, metal, wood, etc.) are illuminated.

However, when the laser pulse hits microparticles of explosives, tiny detonations called microdetonations occur, giving rise to a fast rising optic pulse with a wavelength distribution or pattern of emmisions that are indicative of the explosive type. This difference in characteristics or patterns is exploited by the computer algorithm in conjunction with a database of patterns of previously recorded microdetonations. A match of the pattern in the data aquisition signal with a known pattern can then be used to generate an alarm signal to indicate the presence of explosives on the surface of the object 23 under test.

The main advantages of the present method of detecting explosives are:

Real-time analysis and display of results

Remote sampling of objects

Rapid sampling within seconds

No chemicals or gases required for sampling or analysis

High overall sensitivity compared to wipe analysis of surface residues

While the invention has been particularly shown and described with respect to the preferred embodiment thereof, it will be understood by those skilled in the art that the foregoing and other changes in form and details made therein without departing from the spirit and scope of the invention, which is limited only by the scope of the following claims.

We claim:

1. An apparatus for laser detection of micro-particles of explosive residue on the surface of an object to be inspected, said apparatus comprising:

(a) a laser for generating a beam of coherent light;

(b) optical means for scanning an object to be inspected with said beam of coherent light to induce micro-detonations of said micro-particles of explosive residue;

(c) a detector means for sensing temporal and spectral information of light emitted from the impingement of said beam of coherent light on said object to be inspected during said scan and generating a data acquisition signal therefrom;

(d) data processing means for comparing said temporal and spectral information in said data acquisition signal with one or more empirically obtained patterns of temporal and spectral information derived from laser induced detonation of said microparticles of explosives;

(e) means for generating an alarm signal in the event said temporal and spectral information in said data acquisition signal matches one of said empirically obtained patterns.

2. A method of detecting micro-particles of explosive residue on an object to be inspected with a laser, said method comprising:

(a) generating a beam of coherent light;

(b) scanning an object to be inspected with said beam of coherent light to induce micro-detonation of said microparticles of explosive residue;

(c) sensing the temporal and spectral information of light emitted from the impingement of said beam of coherent light on said object to be inspected during said scan and generating a data acquisition signal therefrom;

(d) comparing said temporal and spectral information in said data acquisition signal with one or more empirically obtained patterns of temporal and spectral information derived from laser induced detonation of said micro-particles of explosives;

(e) generating an alarm signal in the event said temporal and spectral information in said data acquisition signal matches one of said empirically obtained patterns.

\* \* \* \* \*